United States Patent [19]

Hooreman et al.

[11] Patent Number: 4,771,483

[45] Date of Patent: Sep. 20, 1988

[54] PANTS HAVING AN ELASTIC BELT, AND PROCESS FOR THE MANUFACTURE THEREOF

[75] Inventors: Bernard Hooreman, Wervicq-Sud; Didier Kahle, Bondue, both of France

[73] Assignee: Boussac Saint Freres B.S.F., Lille, France

[21] Appl. No.: 842,710

[22] PCT Filed: May 13, 1985

[86] PCT No.: PCT/FR85/00114

§ 371 Date: Jan. 16, 1986

§ 102(e) Date: Jan. 16, 1986

[87] PCT Pub. No.: WO85/05254

PCT Pub. Date: Dec. 5, 1985

[30] Foreign Application Priority Data

May 16, 1984 [FR] France ............................. 84 07909
Jun. 28, 1984 [BE] Belgium .............................. 213234
Oct. 30, 1984 [BE] Belgium .............................. 213923

[51] Int. Cl.⁴ .......................... A41F 9/02; A41B 9/14; A61F 13/16
[52] U.S. Cl. .......................................... 2/237; 2/238; 2/402; 2/403; 2/406; 604/392
[58] Field of Search ................... 2/237, 221, 403, 406, 2/227, 238, 243, DIG. 7, 402; 604/385, 392

[56] References Cited

U.S. PATENT DOCUMENTS

| | | | |
|---|---|---|---|
| 2,408,723 | 10/1946 | Arpin et al. | 2/403 |
| 2,419,867 | 4/1947 | Woodman | 2/403 |
| 3,488,778 | 1/1970 | Gaujon et al. | 2/406 X |
| 3,491,763 | 1/1970 | Osterman et al. | 2/406 X |
| 3,560,292 | 2/1971 | Butler | 2/406 X |
| 4,227,952 | 10/1980 | Sabee . | |
| 4,297,157 | 10/1981 | Van Vliet . | |
| 4,407,284 | 10/1983 | Pieniak . | |

FOREIGN PATENT DOCUMENTS

| | | |
|---|---|---|
| 0048011 | 3/1982 | European Pat. Off. . |
| 91316 | 10/1983 | European Pat. Off. . |
| 145080 | 6/1985 | European Pat. Off. . |
| 157649 | 10/1985 | European Pat. Off. . |
| 2082803 | 11/1971 | France . |
| 2140965 | 12/1972 | France . |
| 2177425 | 11/1973 | France . |
| 2517524 | 6/1983 | France . |
| 2072491 | 10/1981 | United Kingdom . |

*Primary Examiner*—H. Hampton Hunter
*Attorney, Agent, or Firm*—Beveridge, DeGrandi & Weilacher

[57] ABSTRACT

Disclosed are pants formed of a rectangular piece of flexible material. The pants include two elongated elements extending along the longitudinal edges of the piece, provided with elastics which are in stretched conditions and are integral by at least their ends with longitudinal ends of the piece in order to form two elastic belt elements for the slip-shaped pilch.

26 Claims, 3 Drawing Sheets

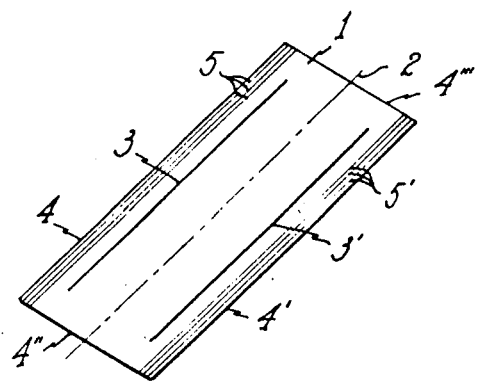
FIG. 1
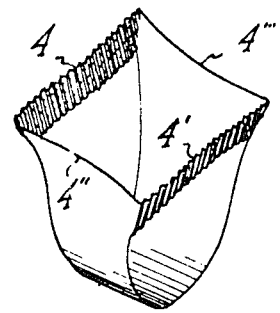
FIG. 2
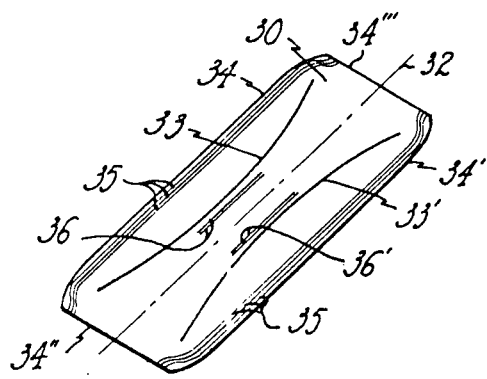
FIG. 3
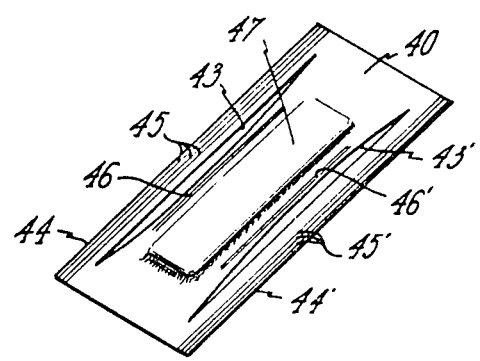
FIG. 4
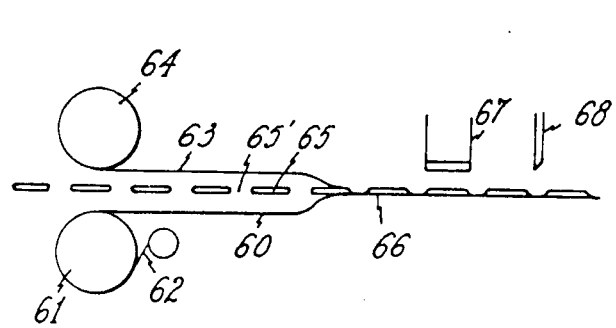
FIG. 6
FIG. 5g
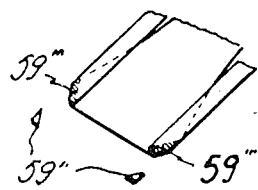
FIG. 5h

PANTS HAVING AN ELASTIC BELT, AND PROCESS FOR THE MANUFACTURE THEREOF

The present invention relates to pants having an elastic belt and produced from a flat piece of flexible material, of rectangular general shape, and to a process for the manufacture of such pants.

The conventional manufacture of articles of clothing of the pants type, whether pants made from textile materials or sanitary articles such as, for example, pilches for incontinent adults or children, requires numerous operations which are ill suited to continuous high-speed manufacture. Problems arise, in particular, in the production of pants having elastic belts. To enable the pants to be continuously manufactured from material in strip form, without interrupting the advancing movement of the strip, elastic belt elements would have to be added or formed in the direction of the movement of the strip, whereas, according to the conventional manufacturing processes, the pants are formed from the strip of material in a manner such that the belt parts are aligned perpendicularly to the direction of movement of the strip.

The subject of the present invention is pants having an elastic belt, of simple design, suitable for continuous high-speed manufacture.

Another subject of the invention is a continuous process for manufacturing pants having an elastic belt, from a material in strip form, according to which process all the operations, and particularly those relating to the attaching of elastic belt elements, can be performed continuously, without interrupting the forward movement of the strip of material.

The pants according to the invention, having an elastic belt, are produced from a flat piece of flexible material, of rectangular general shape. The pants comprise two elastic elements extending, when the said piece of flexible material is laid flat, in the stretched state along the two opposing lengthwise edges of the said piece. The two ends of each of the said elastic elements are attached to the said piece at points situated in the vicinity of the two transverse ends of the latter. Thus the two elastic elements together with the said piece delimit, when the pants in slip form are in the position of use, two apertures for the passage of the legs and form two elastic belt elements at waist height.

On the pants according to the invention, the two elastic belt elements can be formed by elements added to the piece of flexible material, their two ends being fixed to the said piece.

According to another embodiment of the pants according to the invention, the two elastic belt elements are formed by two lengthwise strips delimited, in the material of the said piece, by two partial lengthwise cuts made in the said piece, between the two transverse ends of the latter, set back inwards relative to the opposing lengthwise edges of the said piece.

The elastic elements are advantageously fixed to the piece of flexible material in a mitered manner relative to the corners of this piece.

The process according to the invention for the continuous manufacture of pants consists, according to one embodiment, in:

continuously feeding, in the stretched state, at least one strip of a flexible material, continuously feeding, parallel to the direction of movement of the strip, from either side of the lengthwise median axis of the latter, elastic elements in the stretched state, determining a basic length of the strip corresponding to the length necessary for manufacturing one pair of pants, the strip then being considered as forming a succession of blanks, fixing, to the strip in the stretched state, the elastic elements in the stretched state in the direction of movement of the strip, this fixing taking place at points close to the rear end and front end of each blank, and cutting the strip and the elastic elements in the transverse direction, in the zone of separation between consecutive blanks.

The process according to the invention for the continuous manufacture of pants, in accordance with another embodiment, consists in:

continuously feeding, in the stretched state, at least one strip of a flexible material, continuously feeding, parallel to the direction of movement of the strip, from either side of the lengthwise median axis of the latter, elastic elements in the stretched state slightly set back relative to the lengthwise edges of the strip, determining a basic length of the strip corresponding to the length necessary for manufacturing one pair of pants, the strip then being considered as forming a succession of blanks, continuously fixing, to the strip in the stretched state, the elastic elements in the stretched state in the direction of movement of the strip, making two symmetrical partial cuts in the strip, level with each blank and between the two ends of the latter, set back inwards relative to the said pieces of elastic, these cuts being generally aligned with the lengthwise direction of the strip, cutting the strip and the pieces of elastic in the transverse direction, in the zone of separation between consecutive blanks.

Preferably, the elastic elements are fixed to the strip, at each corner of the blank, in a substantially mitered manner, that is to say substantially perpendicularly to the bisector of the corner in question.

According to another embodiment of the process according to the invention, wedge-shaped cuts are made in the strip, in the front and rear end zones of each blank, on either side of the lengthwise median axis of the strip, to form points at the locations of the corners of the blank portion intended to form the pants, the points thus formed are folded back on the upper surface of the blank, the elastic elements in the stretched state are fixed to the visible surface of the folded-back points, and the definitive shape of the portion of flexible material forming the pants is cut into the strip, within each blank.

For the manufacture of a pilch, it may be advantageous to fix to the strip, over a part of the length of each blank, substantially half-way between the ends of each blank, limited lengths of pieces of elastic in the stretched state, generally aligned with the lengthwise direction of the strip, in the vicinity of the lengthwise edges of the central portion of the flexible material forming the pants.

According to another embodiment, the lengthwise edges of the strip, provided with pieces of elastic and situated outside the cuts, are folded back onto the central part of the blank, and the portions of the flaps located between the ends of the cuts and the corresponding transverse edges of the blank are fixed by mitering to the central part of the blank.

With reference to the attached drawings, a more detailed description of several embodiments of the invention will be given below, by way of illustrative and nonlimiting examples; in the drawing:

FIG. 1 is a perspective view of a simple embodiment of a pair of pants according to the invention, in the stretched state;

FIG. 2 is a view, again in perspective, of the pair of pants shown in FIG. 1, after release of the elastic elements;

FIGS. 3 and 4 are perspective views of two other embodiments of the pair of pants according to the invention, in the stretched state;

FIGS. 5g and 5h are partial perspective views of an alternative embodiment of the stages as illustrated in FIGS. 5d and 5e;

FIG. 6 illustrates diagrammatically a process for the continuous manufacture of pilches according to the invention, provided with absorbent pads;

Figure 5A:
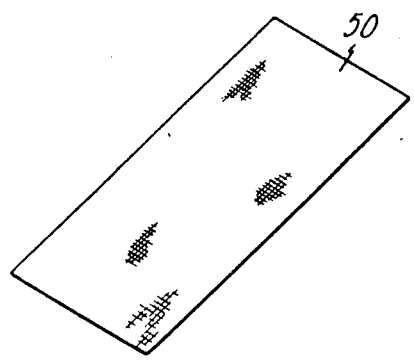
FIGS. 5a to 5e show, in perspective and in the stretched state, a preferred embodiment of a pair of pants according to the invention, at various stages of its manufacture.
Figure 5B:
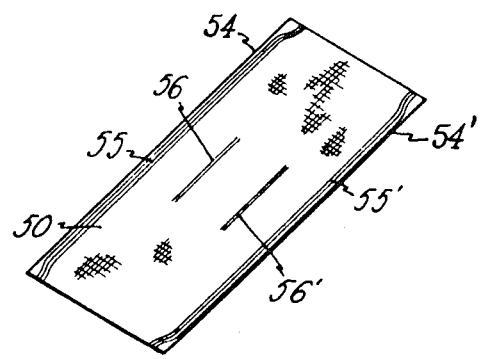
Figure 5C:
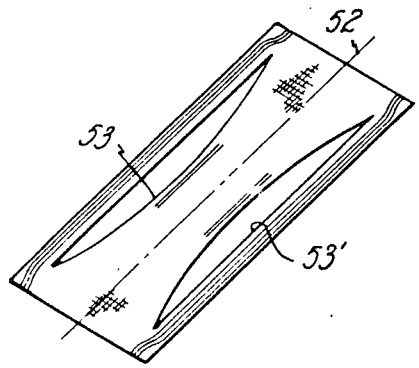

Referring more particularly to FIG. 1, it may be seen that a pair of pants according to the invention, of extremely simple design, essentially comprises a sheet 1, which is plane, flexible, rectangular and hence symmetrical about its lengthwise axis 2, in which sheet partial lengthwise cuts 3, 3' are made in the form of rectilinear slits, which are at least substantially symmetrical about the axis 2. Pieces of elastic 5, 5' extending lengthwise are fixed to the sheet in the zones included between the lengthwise edges 4, 4' and the cuts 3, 3'. The pieces of elastic are fixed to the sheet in the stretched state, over the length of the lengthwise edges 4, 4', in any suitable manner, for example by gluing, welding or sewing.

When the plane piece thus formed, with the pieces of elastic 5, 5', is freed of all stress, the pieces of elastic 5, 5' contract, giving rise to folding of the lengthwise edges 4, 4' of the article, and bringing the article into the shape shown in FIG. 2.

The proportions of the plane piece (length relative to breadth) and the elongation of the pieces of elastic at the time when they are fixed to the sheet are determined so that, at the time of the apparent reduction in the perimeter resulting from the folding of the lengthwise edges, the periphery of the article obtained (lateral edges 4, 4' retracted elastically, and non-elastic transverse edges 4", 4"') forms an elastic belt corresponding to the waist of the pants in question.

A pair of pants of this type can be produced continuously according to a process consisting in continuously feeding, in the stretched state, at least one strip of a flexible material, continuously feeding parallel to the direction of movement of the strip, on either side of the lengthwise median axis of the strip, pieces of elastic in the stretched state, determining a basic length of strip corresponding to the length necessary for the manufacture of an article, the strip then being considered as a succession of article blanks, fixing to the strip in the stretched state pieces of elastic in the stretched state arranged in the direction of movement of the strip, making two cuts in the strip, at the level of each blank and between the two transverse ends of the latter, set back inwards relative to the said pieces of elastic, these cuts being symmetrical about the lengthwise median axis of the strip and being generally aligned according to the direction of this axis, and transversely cutting the strip and the pieces of elastic fixed thereto, in the transverse direction, in the zone of separation between consecutive blanks.

According to the alternative embodiment of FIG. 3, partial cuts 33, 33' are made in an oblong plane piece 30 of flexible material, these cuts being in the form of curvilinear slits and generally symmetrical about the lengthwise axis 32. Pieces of elastic 35, 35' in the stretched state are fixed to the piece 30 in the stretched state, in the zones adjacent to the lengthwise edges 34, 34', so as to form an elastic belt. These pieces of elastic are positioned along a generally rectilinear trajectory, curving inwards at the ends of the plane piece. These arrangements enable the width of the transverse edges 34", 34"' not provided with pieces of elastic to be reduced. Other pieces of elastic 36, 36' are fixed to the plane piece 30, again in the stretched state, in the zones adjacent to the inside edges of the cuts 33, 33', to provide a grip on the legs.

With reference to the alternative embodiment in FIG. 4, this shows a plane piece 40 formed of a multilayer material provided with cuts 43, 43' where material has been removed. These cuts each comprise a rectilinear cut and a curvilinear cut. As in the embodiment shown in FIG. 3, lengthwise pieces of elastic 45, 45' in the stretched state are fixed to the piece 40, in the zone of the lengthwise edges 44, 44', over the entire length, and pieces of elastic 46, 46' in the stretched state are fixed to the piece 40 in the zones adjacent to the inside edges of the cuts 43, 43'. Moreover, the multi-layer material of the plane piece 40 possesses an absorbent pad 47 in the zone situated between the cuts 43, 43'.

FIG. 6 illustrates diagrammatically the implementation of a process according to the invention for the production of a pilch as shown in FIG. 4.

According to this method of implementing the process, the strip of flexible material 60, preferably a plastic material which is impervious to moisture, intended to form the outer sheet of the pilch is continuously fed from the reel 61. For all the subsequent operations, a basic length of strip is determined corresponding to the length of a blank necessary for the production of a pilch. Pieces of elastic 62, in the stretched state, are fixed to the strip, continuously in the zone of the lengthwise edges of the latter, and discontinuously within each blank at the level of the zones provided for the cuts and in the regions of the inside edge of the latter. The strip 60 is kept in the stretched state.

Simultaneously, a second strip 63 of a material which is permeable to moisture, for example a non-woven, is continuously fed from a reel 64, and pads 65 of absorbent material are brought discontinuously, between the two strips 60 and 63, into the zone of the lengthwise median axis of the latter, the said pads being separated by intervals 65' which are necessary to ensure that a pad 65, the length of which is less than the length of the blank, is always located at the same position on the blank. The two strips 60, 63 and the said pads 65 are then fixed together to form a composite material 66 which is kept in the stretched state. A first cutting member 67, acting intermittently, is provided to make the partial lengthwise cuts in the stretched composite material, level with each blank. Then, a second cutting member 68, located transversely to the composite material in strip form, effects the separation, again intermittently, of the various pilches in this strip. After this separation, the tension which was keeping the composite material in the stretched state ceases, so that the pieces of elastic fixed in the stretched state to the composite material contract and thus effect the shaping of the pilches.

FIGS. 5a to 5f illustrate an embodiment of another pair of pants according to the invention, during its various manufacturing stages.

The pants are formed from a rectangular sheet 50 of flexible material (FIG. 5a). During the subsequent stage (FIG. 5b), this sheet 50, kept in the stretched state, is provided, in the zones close to its lengthwise edges 54, 54', with pieces of elastic 55, 55' in the stretched state, and also, in the zone provided for the cuts, in the region of the inner edge of the said zone, with pieces of elastic 56, 56' again in the stretched state. The pieces of elastic 55, 55' and 56, 56' are fixed, for example, by gluing.

Next (FIG. 5c), the sheet 50 with the pieces of elastic 55, 55', 56, 56' fixed thereto being kept in the stretched state, partial lengthwise cuts 53, 53' are made in the sheet 50, these cuts being at least substantially symmetrical about the lengthwise median axis 52.

The sheet 50 remaining in the stretched state, flaps 57, 57' are then formed (FIG. 5d) by folding the zones of the edges located outside the cuts 53, 53' onto the central part of the sheet.

Finally (FIG. 5e), the sheet 50 being kept in the stretched state, the portion of the flap situated between the end 59 of the cut 53, 53' and the corresponding transverse edge 54'' of the sheet is folded back onto the central part, according to the arrow 58, and this folded-back part is fixed, for example by gluing, welding, etc., to the central part.

Figure 5D:
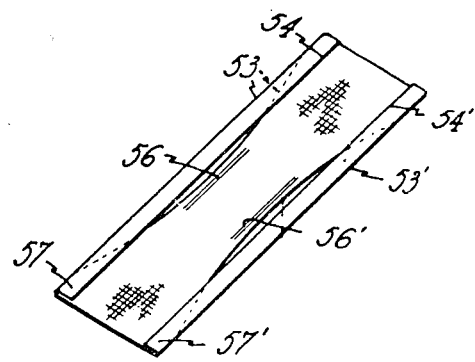
Figure 5E:
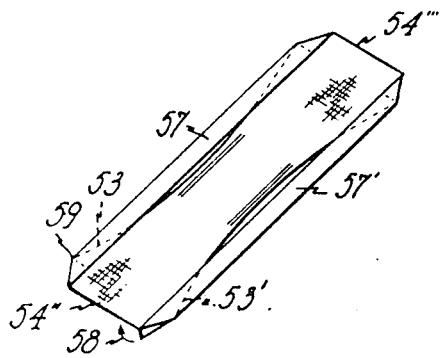
Figure 5F:
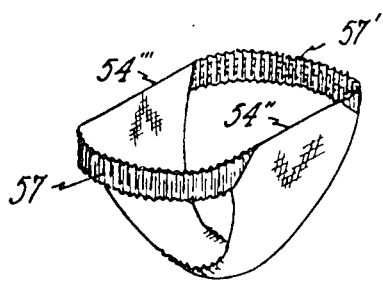
FIG. 5f shows the pants obtained as a result stage 5e, after retraction of the elastic elements.

When the pair of pants thus formed is released, it takes the form shown in FIG. 5f, under the effect of the elastic contraction of the zones 57, 57' possessing the pieces of elastic 55, 55'.

The folding shown in FIGS. 5d and 5e has on the one hand the advantage that, by careful selection of the dimensions of the flaps, the elastic zones 57, 57' of the lengthwise edges 54, 54' are brought into the extension of the transverse edges 54'', 54''', and, on the other hand, the advantage of providing reinforcement of the end 59 of the cuts 53, 53', as well as reducing to a certain extent the apparent perimeter of the article obtained. A pair of pants having a more traditional appearance is thus obtained.

According to the alternative embodiment shown in FIGS. 5g and 5h, a triangular joint 59' is produced by gluing or welding between the end of the flaps 57, 57' and the central portion, the end portion 59'' of this triangular joint surface is then cut to leave a mitered join 59''' substantially at right angles relative to the bisector of the corners of the central portion. The same effect is thus produced, in a technically simple manner, as was described in relation to the embodiment shown in FIGS. 5a to 5f.

It will be noted that, in the manner of operation which has just been described in relation to FIGS. 5a1, 5b, 5c, 5g and 5h, the various operations (fixing of the pieces of elastic, making of the cuts, folding, gluing) are performed following the lengthwise direction of the strip. The design of this product is thus well suited to the process of continuous manufacture of pants from a strip of flexible material.

Figure 7:
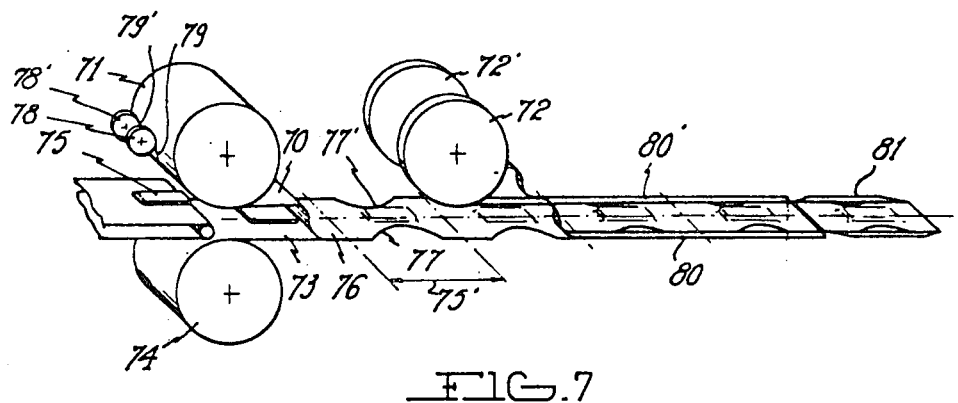
FIG. 7 illustrates diagrammatically an alternative to the process of FIG. 6.

An alternative embodiment of the process for the production of a pilch having the same appearance as the pants illustrated in 5e, but differing in that an absorbent pad is present, is diagrammatically shown in FIG. 7.

According to this embodiment, a strip 73 of a material which is permeable to moisture, for example a nonwoven strip, intended to form the inner surface of the pilch, is continuously fed from a reel 74, and a strip 70 of flexible material which is impervious to moisture, for example plastic material, intended to form the outer surface of the pilch, is continuously fed from a reel 71, while simultaneously absorbent pads 75 are discontinuously brought between the two strips. Pieces of elastic 79, 79', continuously unrolled in the stretched state from reels 78, 78' are intermittently fixed in the stretched state to the strip 70 at locations positioned laterally on either side of the locations intended to receive the pads 75. The whole is then fixed together in the form of a strip of composite material 76 which is kept in the stretched state. In order to fix the pieces of elastic 78, 78', and also to fix the rate of introduction of the pads 75 and for all the subsequent operations, a basic length of strip 75' is determined, corresponding to the length of a blank necessary for the production of a pilch, the strip then being considered as a series of blanks, the boundary between the consecutive blanks being shown in dot-and-dash lines in the drawing.

Two cuts 77, 77' are then made in the strip 76, level with the central part of each blank, in the form of an arcuate indentation which is generally symmetrical about the lengthwise axis of the strip, in order to give the blank the general shape of an hourglass. Subsequently, elastic elements 80, 80' in the stretched state are continuously unrolled from two reels 72, 72'. These elastic elements are each formed from a strip of flexible material to which pieces of elastic in the stretched state are fixed. The elastic elements 80, 80' in the stretched state are superposed on the lengthwise edges of the strip 76, and fixed to the blanks which this strip forms, at each corner of the said blanks. As in the embodiment shown in FIGS. 5g and 5h, the fixing of the elastic elements 80, 80' is performed by mitered welding relative to the corners of the blanks, that is to say substantially at right angles relative to the bisector of each corner. In the course of this fixing operation, the surplus of welded or glued material forming the corners of the blank is cut off and the finished article 81 is separated from the end of the strip.

Figure 10:
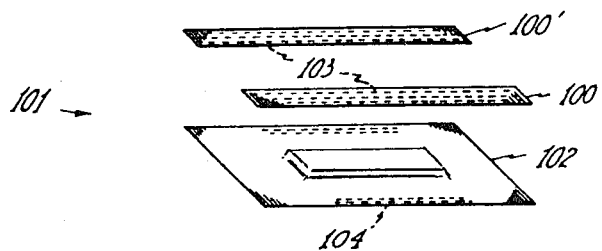
FIG. 10 is an exploded view of a pilch according to the invention, of a simple type, the various component elements being shown in the stretched state.

It is appropriate to note that the cuts 77, 77' in the form of arcuate indentations can also be omitted, in order to obtain an article of simpler design, of rectangular shape. An article of this type is illustrated in FIG. 10. This article is made up of two elastic belt elements 100, 100' fixed to a plane piece 102 of rectangular shape, made up of a sheet which is impervious to moisture, an absorbent pad and a sheet which is permeable to moisture. The pieces of elastic 103 in the elastic belt elements 100, 100', and the pieces of elastic 104 fixed to the piece 102 to provide an elastic grip for the passage of the legs, are shown in dotted lines. The triangular zones for fixing the elastic elements 100, 100' to the corners of the piece 102 are indicated by cross-hatching. The passages for the legs are formed between the intermediate free parts of the elastic elements 100,100' and the piece 102.

Figure 8A:
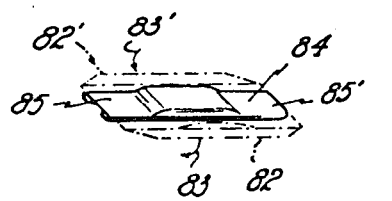
FIGS. 8a and 8b show the successive stages of folding a pilch according to FIGS. 5e, 5h, or a pilch obtained by the process according to FIG. 7.
Figure 8B:
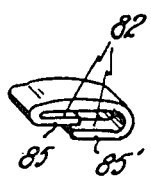
Figure 8C:

FIGS. 8a and 8b illustrate a method of folding the finished pilch 81 of FIG. 7, which on the one hand permits convenient individual packaging and on the other hand enables the pilch to be reversed to bring it into the state shown in FIG. 8c, namely a state where the impervious flexible material 70 forms the exterior of the pilch. In fact, following the process illustrated in FIG. 7, if the finished product 81 is released, the tension of the elastic belt elements 80, 80' situated on top of the strip of flexible material 70 tends to bend the finished product in a manner such that the strip 70 forms the inner surface of the product. To avoid this effect, the finished article 81 is folded lengthwise to form two lateral flaps 82, 82' which are brought, following the direction of the arrows 83, 83', below the surface formed by the permeable sheet 73. Releasing of the pieces of elastic will then bring about the curvature of the article 81 in a manner such that the permeable sheet 73 forms the internal surface of the article. This tendency will be further encouraged, and packaging made easier, if the article undergoes a further transverse folding to form two complementary flaps 85, 85' (FIG. 8b).

Figure 9:
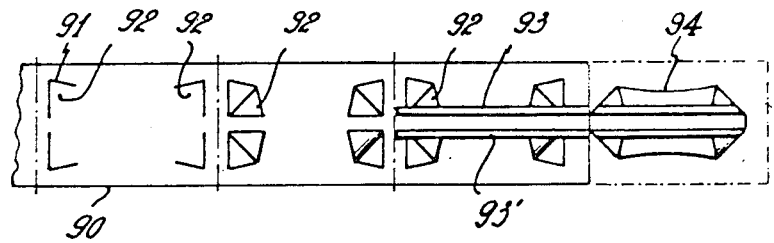
FIG. 9 shows diagrammatically the stages of a manufacturing process according to the invention, enabling pants of another type to be obtained.

Finally, FIG. 9 illustrates diagrammatically the stages of a process making it possible to obtain pants of a different type.

According to this process, wedge-shaped cuts 91 are made in the strip 90, in the zones of the front and rear ends of each blank, to form points 92 for the locations of the corners of the plane piece forming the pants. The corners 92 are then folded back on the strip 90, so that the portions of the corners of the plane piece which are normally located in the transverse direction are, after the folding back, again aligned with the lengthwise direction of the strip 90. Elastic elements 93, 93' in the stretched state are then fixed, in the lengthwise direction of the strip, to the folded-back points 92. Finally, the definitive shape of the flat piece forming the pants is cut out from the strip 90, following the outline 94, which in itself results in the cutting-off of the surplus of the elastic elements beyond the folded-back points, and the article obtained is released. According to the invention, the strip 90 to which the elastic elements are fixed is kept in the stretched state until production of the finished article is complete.

It is self-evident that any suitable material may be used for the flexible sheet from which the pants are produced, for example a woven or non-woven textile material. However, the invention is particularly suitable for the production of disposable pants made from non-woven material. Similarly, in view of the simplicity of carrying out the process with the aid of composite materials, and the retail price resulting from the high speed of production thus permitted, the invention is ideally suited for the production of sanitary articles such as pilches, pants for incontinent adults, and other similar sanitary articles. During the production of pilches, which here take the form of slips, it is advantageous to provide weakened zones in the belt, enabling the belt to be torn, in order to enable the pilch to be opened and removed in a conventional manner when soiled.

We claim:

1. An article of clothing of the pants type comprising: a generally rectangular piece of flexible sheet material having all of its edges in substantially straight line form when said piece of sheet material is in a plane state; a first and a second elastic element secured to said piece of material, said first elastic element and said second elastic element positioned along the two opposite lengthwise edges of said generally rectangular piece of material, the two ends of each of said first and second elastic elements being secured to said piece of material at positions located in the vicinity of the two transversely extending edges forming the ends of said generally rectangular piece of material, and said rectangular sheet of material having two partial lengthwise cuts between the transverse edges forming the ends of said piece of material and set back inwards relative to the opposite lengthwise inside edges of said elastic elements.

2. An article of clothing as recited in claim 1 wherein said first and second elastic elements secured to said piece of material are in a tensioned or stretched state when said flexible sheet of material is in a plane state.

3. An article of clothing as recited in claim 2 wherein each of said first and second elastic elements are formed of an elongate, relatively narrow length of elastic material.

4. An article of clothing as recited in claim 1 wherein said lengthwise cuts are symmetrical about the lengthwise median axis of said piece of material and aligned parallel to said axis.

5. An article of clothing as recited in claim 1 wherein said generally rectangular piece of material has rounded corners, and said lengthwise cuts being in the form of outwardly extending curvilinear slits positioned generally symmetrical about the lengthwise median axis of said piece of material.

6. An article of clothing as recited in claim 5 wherein said first and second elastic elements have curved ends which conform substantially with the curvature of said rounded corners of said generally rectangular piece of material.

7. An article of clothing as recited in claim 5 further comprising third and fourth elastic elements; said third and fourth elastic elements being positioned on the same plane of said piece of material as that of said first and second elements, said third and fourth elastic elements being positioned so as to be symmetrical about the lengthwise median axis of said piece of material, said third and fourth elastic elements being of a length that is less than that of said first and second elastic elements, and said third elastic element being positioned so as to have its intermediate section lie inside of the innermost point of one of the two curvalinear slits while said fourth element has it intermediate section positioned just inside the innermost point of the second of the two curvalinear slits.

8. An article of clothing as recited in claim 4 wherein said piece of material is formed of multiple layers.

9. An article of clothing as recited in claim 8 further comprising two outwardly extending curvilinear cuts positioned symmetrically about the lengthwise median axis of said piece of material and having ends corresponding with the ends of said cuts aligned parallel with said axis so as to form a cutout therebetween.

10. An article of clothing as recited in claim 9 further comprising an absorbent pad securely positioned between said multiple layers in the general area between said cutouts.

11. An article of clothing as recited in claim 10 further comprising third and fourth elastic elements; said third and fourth elastic elements being positioned on the same plane of said piece of material as that of said first and second elements, said third and fourth elastic elements being positioned so as to by symmetrical about the lengthwise median axis of said piece of material, said third and fourth elastic element being of a length that is less than that of said first and second elastic elements and said third elastic element being positioned so as to have its intermediate section lie just inside of the innermost point of one of the two curviliear cuts while said fourth element has its intermediate section positioned just inside the innermost point of the other of the two curvilinear cuts.

12. Process for the continued manufacture of pants from a flexible material; said process comprising:
   continuously feeding at least one strip of a flexible material in a stretched state,
   feeding parallel to the direction of movement of said strip, on each side of the lengthwise median axis of said strip, an elastic element also in a stretched state,
   determining a basic length of said strip which corresponds to the length required for a desired size pair of pants, the strip than being considered as forming a series of blanks with each blank having said basic length,
   fixing said elastic elements to said strip while both said strip and said elastic element are in a stretched state, said fixing of said elastic elements to said strip taking place at points close to the rear end and front end of each of said blanks,
   and cutting said strip an said elastic elements in a direction transverse to a direction of movement of said strip in a zone of separation between consecutive blanks.

13. A process as recited in claim 12 further comprising the making of two symmetrical partial cuts in said strip such that each cut is generally aligned with the lengthwise direction of said strip and each cut is positioned between the ends of each blank.

14. Process for the continuous manufacture of pants from a flexible material; said process comprising:
   continuously feeding at least one strip of flexible material in a stretched state,
   continuously feeding, parallel to said at least one strip, elastic elements each of which is in a stretched state,
   feeding said elastic elements from either side of the median lengthwise axis of said at least one strip, so as to be slightly set back relative to the lengthwise edges of said strip,
   determining a basic length of said strip which corresponds to the length required for a desired size pair of pants, said strip being considered as forming a succession of blanks,
   continuously fixing said strip to said elastic elements while each are in a stretched state,
   making two symmetrical partial cuts in said strip such that each cut is generally aligned with the lengthwise direction of said strip and each cut is positioned so as to be between the ends of each blank,
   cutting said strip and said elastic elements in a direction transverse to a direction of movement of said strip in a zone of separation between consecutive blanks.

15. Process as claimed in claim 12 or 14 wherein the elastic elements are fixed to said strip at each corner of one of said blanks in a substantially mitered manner relative to each of said corners.

16. A process as claimed in claim 12 including making wedge shaped cuts in said strip in the front and rear areas of each of said blanks on each side of the lengthwise median axis of said strip, said wedge shaped cuts being arranged so as to have the points formed by said wedge shaped cuts positioned in the vicinity of the corners of each of said blanks, folding each portion of said strip lying within the boundaries of said wedge shaped cutout away from the corners of said blanks and onto the upper surface of said blanks, fixing said elastic elements in their stretched shape to the visible portion of the folded over portions of said strip and cutting into said strip within each of said blanks the definitive shape of the portion of flexible material forming the pants.

17. Process as claimed in claim 13 or 14, including fixing limited lengths of pieces of elastic in a stretched state to said strip, over part of the length of each blank, at a position substantially half-way between the ends of each of said blanks, said pieces arranged symmetrically about the median lengthwise axis of said strip in a generally parallel alignment with said axis in the vicinity of the lengthwise edges of a central piece of flexible material formed between said two partial cuts made in each blank.

18. Process as claimed in claim 14, including folding back the lengthwise edges of said strip so that over the central portion of each of said blanks the folded back edges of said strip lie outside said cuts, providing said folded back edges with pieces of elastic, mitering the portions of said folded back edges located between the ends of the cuts and the corresponding transverse edges of each of said blanks to the central portion of each of said blanks.

19. Process as claimed in claim 15, including fixing limited lengths of pieces of elastic in a stretched state to said strip, over part of the length of each blank at a position substantially half-way between the ends of each of said blanks, arranging said pieces symmetrically about the median lengthwise axis of said strip in a generally parallel alignment with said axis in the vicinity of the lengthwise edges of a central piece of flexible material formed between said two partial cuts made in each blank.

20. An article of clothing as claimed in claim 1 wherein the elastic elements are fixed to the piece of material in a mitered manner relative to the corners of said piece of material.

21. An article of clothing of the pants type comprising:
   a generally rectangular piece of flexible sheet material having formed therein and set back inwards relative to the opposite lengthwise edges of said piece of material, two partial lengthwise cuts made between the transverse edges forming the ends of said piece of material, thus defining a central portion and two side portions integral with the central portion in the vicinity of said two transverse edges; and
   first and second elastic elements secured in a stretched state and in a lengthwise condition on said two side portions, respectively, at a time when said piece of sheet material is in a plane state.

22. An article of clothing as recited in claim 21 wherein said piece of material is formed of multiple layers and said article further comprises:
- an absorbent pad positioned in said central portion between two of said multiple layers; and
- third and fourth elastic elements secured in a stretched state and in a lengthwise condition on said central portion of said flexible sheet of material between a respective one of the cuts formed in said flexible sheet of material and the edge of said absorbent pad closest to that cut.

23. An article of clothing of the pants type, comprising:
- a generally rectangular piece of flexible sheet material, said piece of sheet material being formed of multiple layers,
- an absorbent pad positioned between said multiple layers of said piece of sheet material,
- two stips of flexible sheet material extending lengthwise over said piece of sheet material along the two lengthwise edges thereof, respectively, and being fixed to said piece of sheet material in the vicinity of the two transverse edges thereof,
- first and second elastic elements extending lengthwise along and fixed in stretched state to said strips, respectively, when said strips are in a plane state, and
- third and fourth elastic elements fixed in a stretched state and in a lengthwise condition to said piece of material, when said piece of material is in a plane state, so as to be between the lengthwise edges of said piece of material and a respective opposite edge of said absorbent pad.

24. An article of clothing as recited in claim 1 wherein said first and second elastic elements secured to said piece of material, are secured along their entire length.

25. An article of cloting of the pants type, comprising;
- a generally rectangular piece of flexible material having substantially straight line edges;
- two elastic belt elements extending lengthwise over said piece of flexible material along a respective one of the lengthwise edges of said piece of flexible material, said elastic belt elements being fixed solely at their ends to a respective corner of said piece of flexible material; and
- first and second elastic elements secured to said piece of flexible material along a respective one of the lengthwise edges of said piece of flexible material such that said first and second elastic elements are positioned directly below a respective one of said elastic belt elements when said belt elements are in a plane state.

26. An article of clothing as recited in claim 25, wherein said piece of material is formed of multiple layers and said article further comprises an absorbent pad positioned between two of said multiple layers.

* * * * *